United States Patent
del Real Pena et al.

(10) Patent No.: US 11,686,425 B2
(45) Date of Patent: Jun. 27, 2023

(54) MECHANICAL LIFTS AND RELATED METHODS OF LIFTING MEDICAL FLUID CONTAINERS

(71) Applicant: Fresenius Medical Care Holdings, Inc., Waltham, MA (US)

(72) Inventors: Diego Suarez del Real Pena, Mission, TX (US); Irving Uziel Hernandez, Rio Bravo (MX); Orestes Soto Ramirez, Reynosa (MX)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 6 days.

(21) Appl. No.: 17/314,818

(22) Filed: May 7, 2021

(65) Prior Publication Data

US 2022/0356981 A1 Nov. 10, 2022

(51) Int. Cl.
*F16M 11/04* (2006.01)
*A61M 5/14* (2006.01)

(52) U.S. Cl.
CPC ........ *F16M 11/046* (2013.01); *A61M 5/1415* (2013.01); *A61M 5/1417* (2013.01); *A61M 5/14* (2013.01); *F16M 2200/028* (2013.01)

(58) Field of Classification Search
CPC ................ F16M 11/046; F16M 11/04; F16M 2200/028; A61M 5/1415; A61M 5/1417; A61M 5/14
USPC .... 248/125.8, 157, 158, 161, 407, 159, 423, 248/295.11, 297.11, 297.31, 304, 307
See application file for complete search history.

(56) References Cited

U.S. PATENT DOCUMENTS 1,755,453 A * 4/1930 Mullen ............... E04D 13/0722
    248/48.1
3,242,924 A * 3/1966 Kraft ................... A61M 39/281
    604/245

(Continued)

FOREIGN PATENT DOCUMENTS

CN    105771023    7/2016
CN    107185074    9/2017

(Continued)

OTHER PUBLICATIONS

International Search Report and Written Opinion in International Appln. No. PCT/US2022/024370, daated Jul. 19, 2022, 13 pages.

*Primary Examiner* — Nkeisha Smith
(74) *Attorney, Agent, or Firm* — Fish & Richardson P.C.

(57) ABSTRACT

A mechanical lift includes a housing defining a series of vertical adjustment notches, an adjustment block disposed within the housing, a hook extending from the adjustment block and configured to support a hanging load, a stopper supported by the adjustment block and movable between retracted and extended positions, and a spring disposed within the housing and exerting an upward force against the adjustment block to mechanically lift the adjustment block and the hook extending therefrom from a first vertical position at a first notch of the series of vertical adjustment notches to a second notch of the series of vertical adjustment notches when the stopper is in the retracted position. In the retracted position, the stopper is disengaged from the housing. In the extended position, the stopper is engaged with a selected notch to lock a vertical position of the adjustment block and the hook extending therefrom.

25 Claims, 8 Drawing Sheets

(56) References Cited

U.S. PATENT DOCUMENTS

| | | | | |
|---|---|---|---|---|
| 3,472,476 A * | 10/1969 | Johnson | A47B 57/562 | 248/245 |
| 3,878,573 A * | 4/1975 | Boudewyn | A61G 7/0506 | 248/362 |
| 4,332,363 A * | 6/1982 | Ware | F16M 11/046 | 362/418 |
| 4,738,487 A * | 4/1988 | Shalinsky | A47C 9/025 | 248/629 |
| 4,883,282 A * | 11/1989 | Wolf | A61H 3/04 | 248/205.8 |
| 4,948,207 A * | 8/1990 | Rolls | A47B 57/00 | 248/188.4 |
| 5,188,323 A * | 2/1993 | David | A61M 5/1415 | 74/110 |
| 5,645,272 A * | 7/1997 | Brennan, Sr. | B25H 1/00 | 269/68 |
| 5,727,764 A * | 3/1998 | Angeles | A47B 57/482 | 248/295.11 |
| 6,017,009 A * | 1/2000 | Swartz | A47B 57/10 | 248/245 |
| 6,378,816 B1 * | 4/2002 | Pfister | F16C 29/04 | 248/161 |
| 6,422,957 B1 * | 7/2002 | Winter | A63B 63/083 | 473/483 |
| 6,802,089 B2 * | 10/2004 | Cropelli | E03C 1/066 | 4/570 |
| 7,624,953 B2 * | 12/2009 | Silverman | A61M 5/1415 | 248/129 |
| 8,056,870 B2 * | 11/2011 | Chih | F16M 11/10 | 248/157 |
| 8,081,431 B2 * | 12/2011 | Fan | F16M 11/24 | 248/920 |
| 8,659,884 B2 * | 2/2014 | Segar | F16M 11/22 | 361/679.22 |
| 9,074,726 B2 * | 7/2015 | Altshuler | F16M 11/18 | |
| 10,119,651 B2 * | 11/2018 | Piovan | F16M 11/048 | |
| 10,299,875 B2 * | 5/2019 | Schoenig | F16M 11/42 | |
| 10,905,864 B2 * | 2/2021 | Mansson | A61M 3/0216 | |
| 11,154,980 B2 * | 10/2021 | Wang | B25H 5/00 | |
| 11,262,176 B2 * | 3/2022 | Wang | G01S 7/40 | |
| 2007/0125916 A1 * | 6/2007 | Cullom | H02G 1/00 | 248/161 |
| 2016/0014920 A1 * | 1/2016 | Hsu | H05K 5/0234 | 248/542 |
| 2016/0157951 A1 * | 6/2016 | Schoenig | F16M 11/38 | 280/47.35 |
| 2017/0159873 A1 * | 6/2017 | Farrell | F16M 11/046 | |
| 2018/0076607 A1 * | 3/2018 | Chatman | H02G 3/32 | |
| 2021/0396348 A1 * | 12/2021 | Chen | F16M 11/28 | |
| 2022/0054099 A1 * | 2/2022 | Han | F16M 11/046 | |
| 2022/0107049 A1 * | 4/2022 | Liu | F16B 2/185 | |

FOREIGN PATENT DOCUMENTS

| | | |
|---|---|---|
| CN | 108543147 | 9/2018 |
| CN | 110585510 | 12/2019 |

\* cited by examiner

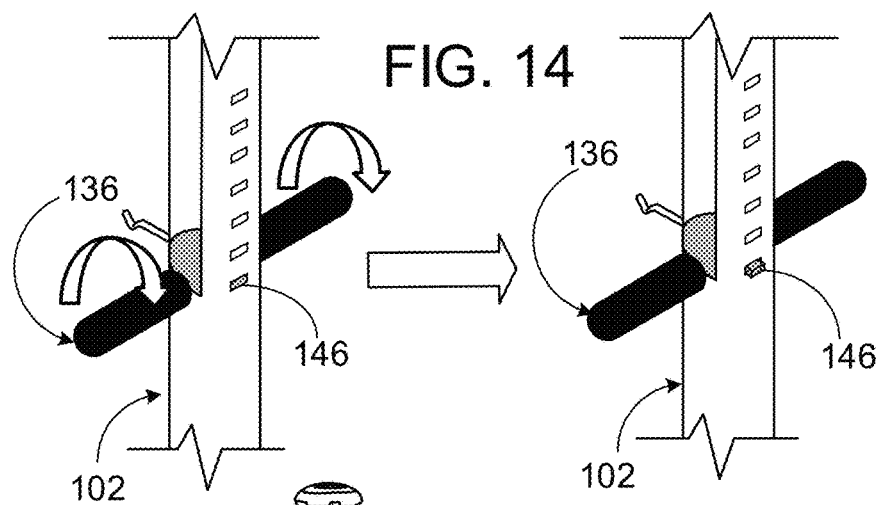
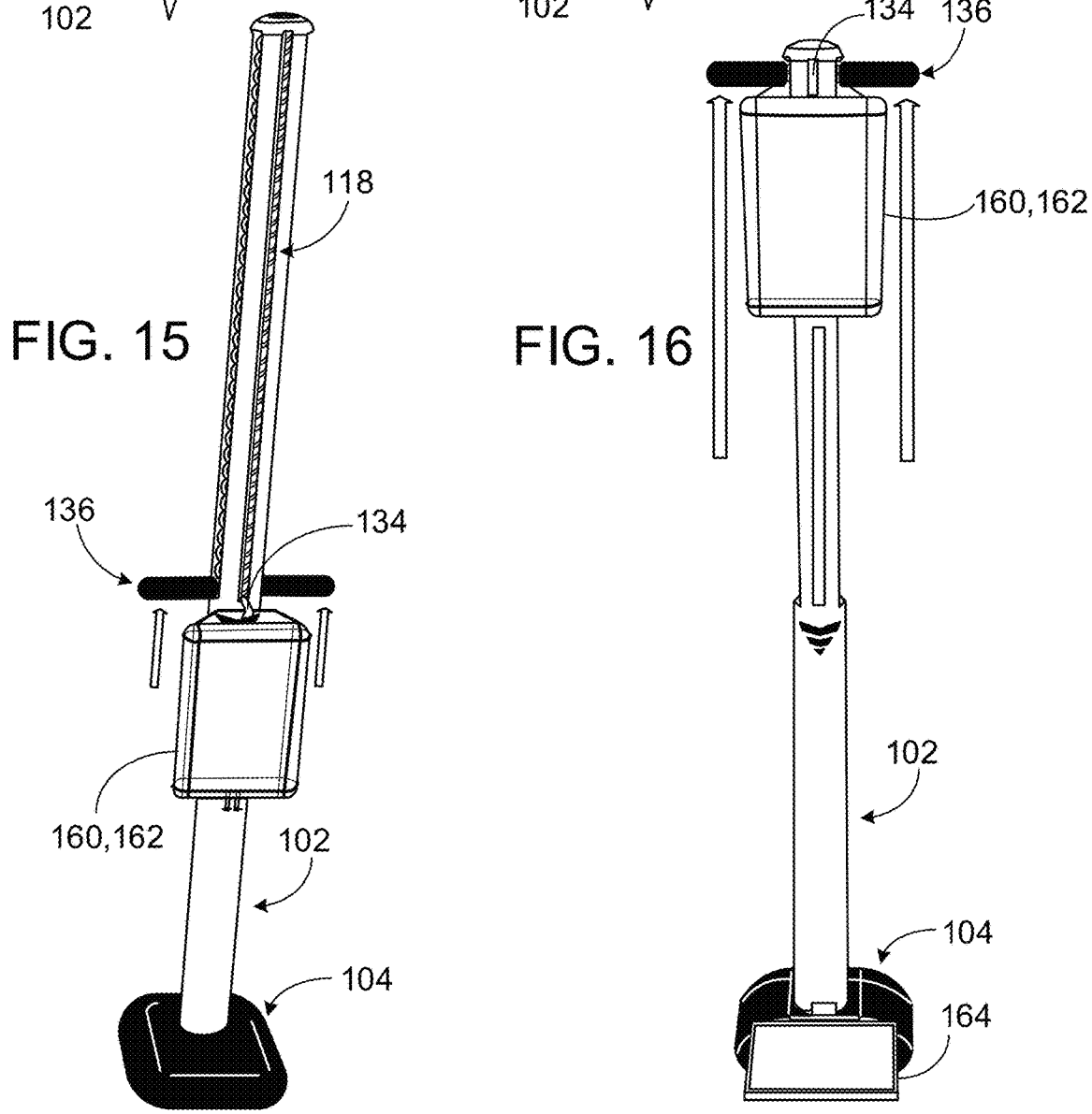

MECHANICAL LIFTS AND RELATED METHODS OF LIFTING MEDICAL FLUID CONTAINERS

TECHNICAL FIELD

This disclosure relates to a mechanical lift that is designed to mechanically lift a container of fluid, such as a mechanical intravenous (IV) pole for lifting a bag of medical fluid.

BACKGROUND

Conventional IV poles require users to lift heavy medical fluid bags above their heads to hook the fluid bags onto a pole. In some examples, such medical fluid bags may have a mass of greater than 5 kg. A patient who receives dialysis treatments due to chronic kidney disease may be required to lift and hang over 1,000 solution bags (e.g., with each bag weighing 5 kg) on a yearly basis, which contributes significantly to patient injury and discomfort.

SUMMARY

In general, this disclosure relates to a mechanical lift that is designed to mechanically lift a container of fluid that is supported by the mechanical lift. For example, the mechanical lift may be embodied as an IV pole that mechanically raises a bag of medical fluid (e.g., a dialysis solution) to prevent a user from having to physically bear the weight of the bag at an uncomfortable height.

In one aspect, a mechanical lift includes a housing defining a series of vertical adjustment notches, an adjustment block disposed within the housing, a hook extending from the adjustment block and configured to support a hanging load, a stopper supported by the adjustment block, and a spring disposed within the housing and exerting an upward force against the adjustment block to mechanically lift the adjustment block and the hook extending therefrom from a first vertical position at a first notch of the series of vertical adjustment notches to a second notch of the series of vertical adjustment notches when the stopper is in the retracted position. The stopper is movable between a retracted position and an extended position. In the retracted position, the stopper is disposed within the adjustment block and is disengaged from the housing. In the extended position, the stopper extends from the adjustment block and is engaged with a selected notch of the series of vertical adjustment notches of the housing to lock a vertical position of the adjustment block and the hook extending therefrom.

Embodiments may provide one or more of the following features.

In some embodiments, the mechanical lift further includes a handle supported on the adjustment block.

In some embodiments, the handle is pivotably coupled to the stopper such that rotation of the handle causes movement of the stopper between the retracted position and the extended position.

In some embodiments, the mechanical lift further includes one or more pivotable arms that couple the handle to the stopper.

In some embodiments, the series of vertical adjustment notches includes a series of slots.

In some embodiments, the stopper is configured to pass through the selected notch.

In some embodiments, the housing defines an opening through which the adjustment block and the spring are viewable.

In some embodiments, the hook extends from a first side of the adjustment block and the stopper extends from a second side of the adjustment block that is opposite to the first side.

In some embodiments, the lowest notch of the series of vertical adjustment notches is located at a distance of about 0.9 m to about 1.1 m above a bottom end of the mechanical lift, and the highest notch of the series of vertical adjustment notches is located at a distance of about 1.9 m to about 2.0 m above the bottom end of the mechanical lift.

In some embodiments, the vertical adjustment notches of the series are equally spaced from each other by a distance of about 1.5 cm to about 3.8 cm.

In some embodiments, the spring is a compression spring that is compressible to locate the adjustment block at the first notch.

In some embodiments, the spring is calibrated to the hanging load.

In some embodiments, the hanging load includes a container of fluid.

In some embodiments, the container of fluid includes a bag of medical fluid.

In some embodiments, the mechanical lift further includes a platform that supports the housing.

In another aspect, a method of positioning a load includes providing a mechanical lift. The mechanical lift includes a housing defining a series of vertical adjustment notches, an adjustment block disposed within the housing, a hook extending from the adjustment block and configured to support the load, a stopper supported by the adjustment block, and a spring disposed within the housing and exerting an upward force against the adjustment block. The method further includes moving the stopper to an extended position with respect to the adjustment block to engage the stopper with a first notch of the series of vertical adjustment notches of the housing to lock the adjustment block and the hook extending therefrom at a first vertical position of the first notch, hanging the load on the hook, moving the stopper from the extended position to a retracted position within the adjustment block to disengage the stopper from the housing, and extending the spring to mechanically lift the adjustment block and the load hanging from the hook from the first vertical position to a second vertical position of a second notch of the series of vertical adjustment notches.

In some embodiments, the mechanical lift further includes a handle supported on the adjustment block, and the handle is pivotably coupled to the stopper.

In some embodiments, the method includes rotating the handle to move the stopper from the extended position to the retracted position.

In some embodiments, the method further includes moving the stopper to the extended position at the second vertical position to engage the stopper with the second notch to lock the adjustment block and the load hanging from the hook at the second vertical position.

In some embodiments, the method further includes moving the adjustment block downward to the first vertical position, compressing the spring prior to moving the stopper to the retracted position, and locking the adjustment block and the hook extending therefrom at the first vertical position.

In some embodiments, the load includes a bag of medical fluid.

The mechanical lift disclosed herein provides several advantages with respect to conventional IV poles. For example, a mechanism of the mechanical lift reduces muscle activity that the user would otherwise undergo to lift a container of fluid and accordingly allows for improved posture and a reduced likelihood of lift-related injuries. The mechanical lift is also ergonomic and user-friendly in that it provides for easy lifting, hanging, and disposal of the container. In this regard, the design of the mechanical lift also reduces the probability that the user will a drop filled container to a floor, which can lead to wasted medical fluids, damage to the floor, or injury related to slipping on a wet floor or mechanical trauma to the user. In preventing these undesirable outcomes, the mechanical lift also avoids added costs that would otherwise be associated with such outcomes.

DESCRIPTION OF DRAWINGS

FIGS. 12-16 illustrate a sequential method of operating the mechanical lift of FIG. 1 to position a container of fluid at the mechanical lift.

DETAILED DESCRIPTION

Figure 1:
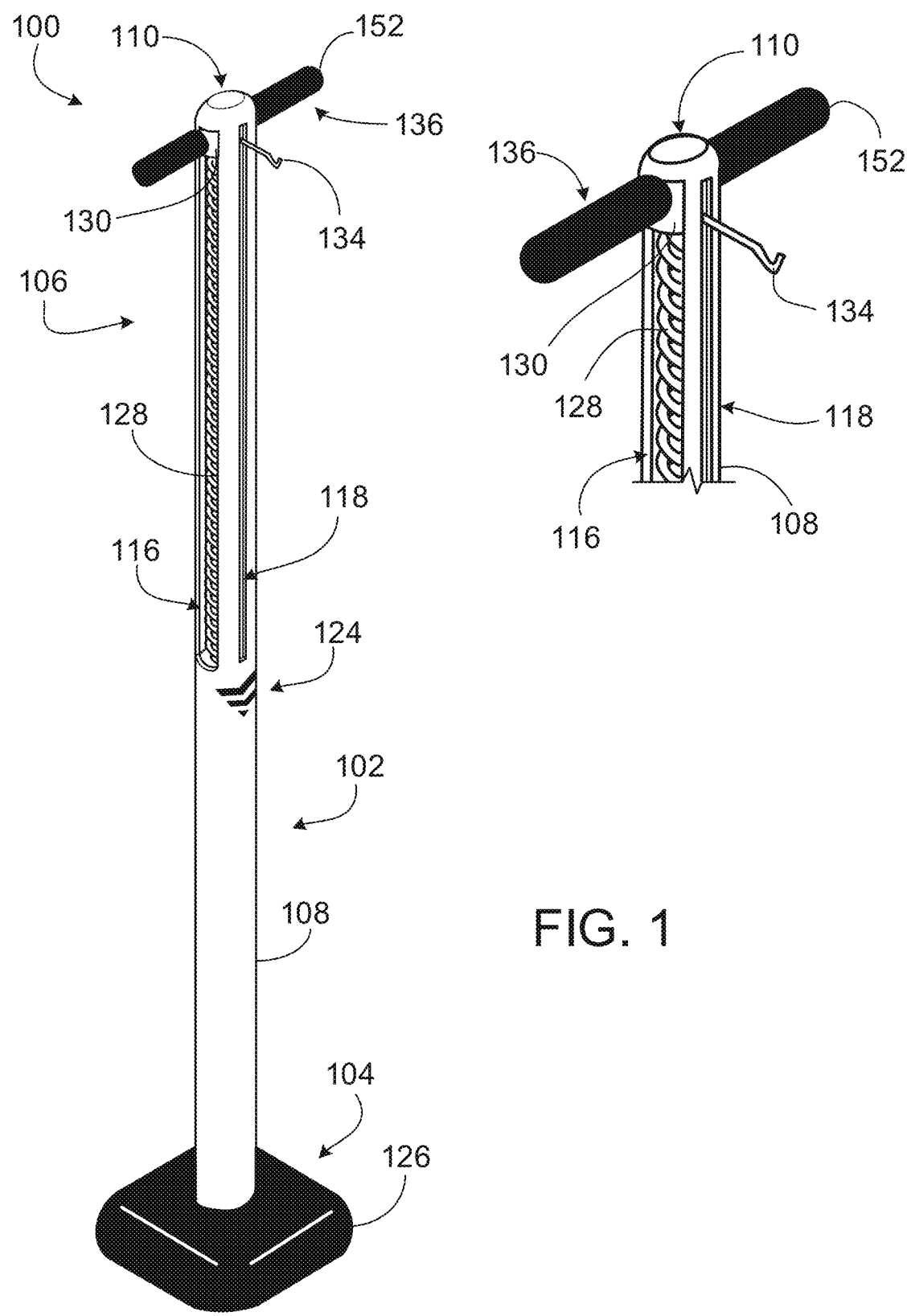
FIG. 1 is a perspective view of a mechanical lift.
Figure 2:
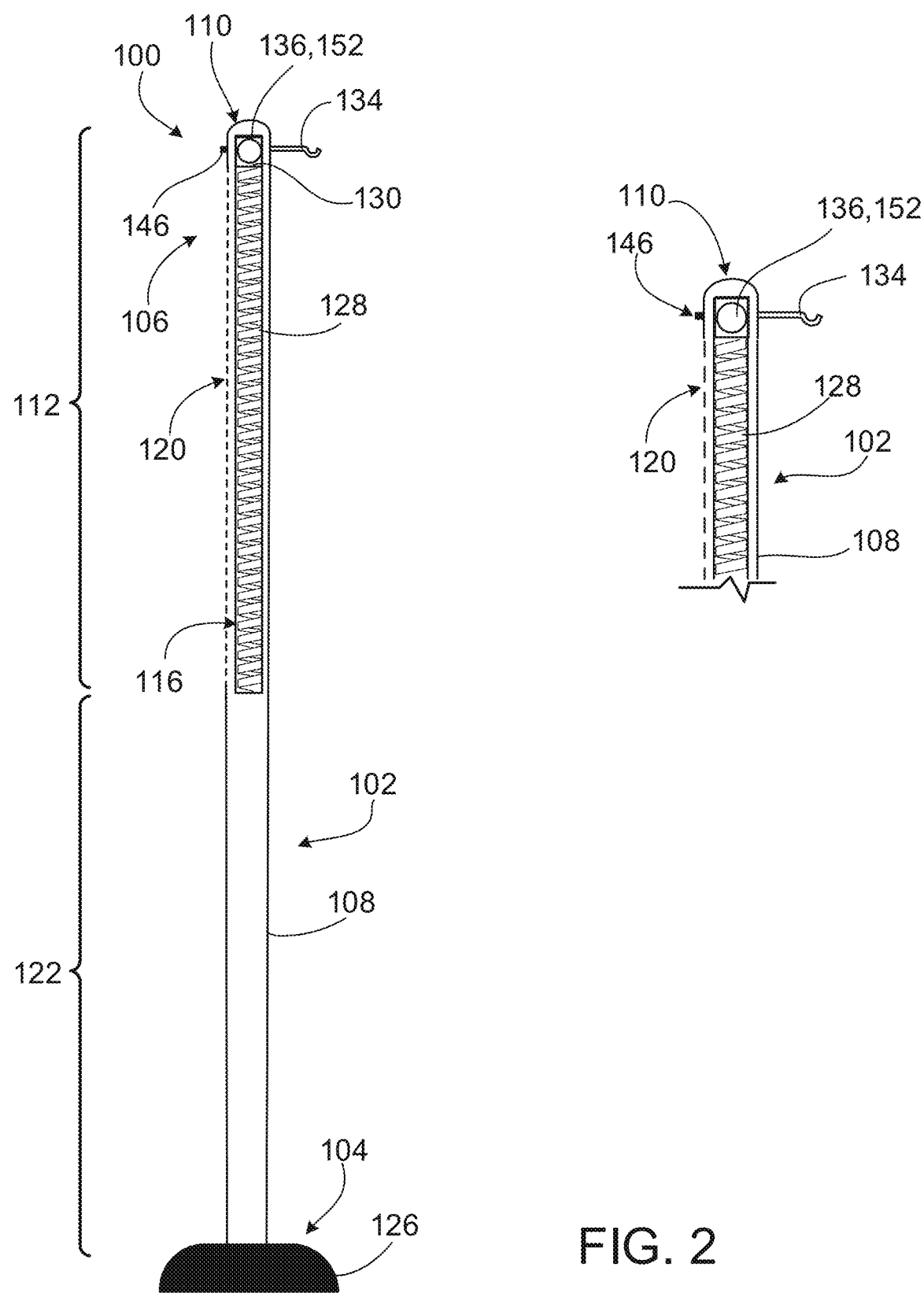
FIG. 2 is a side view of the mechanical lift of FIG. 1.
Figure 3:
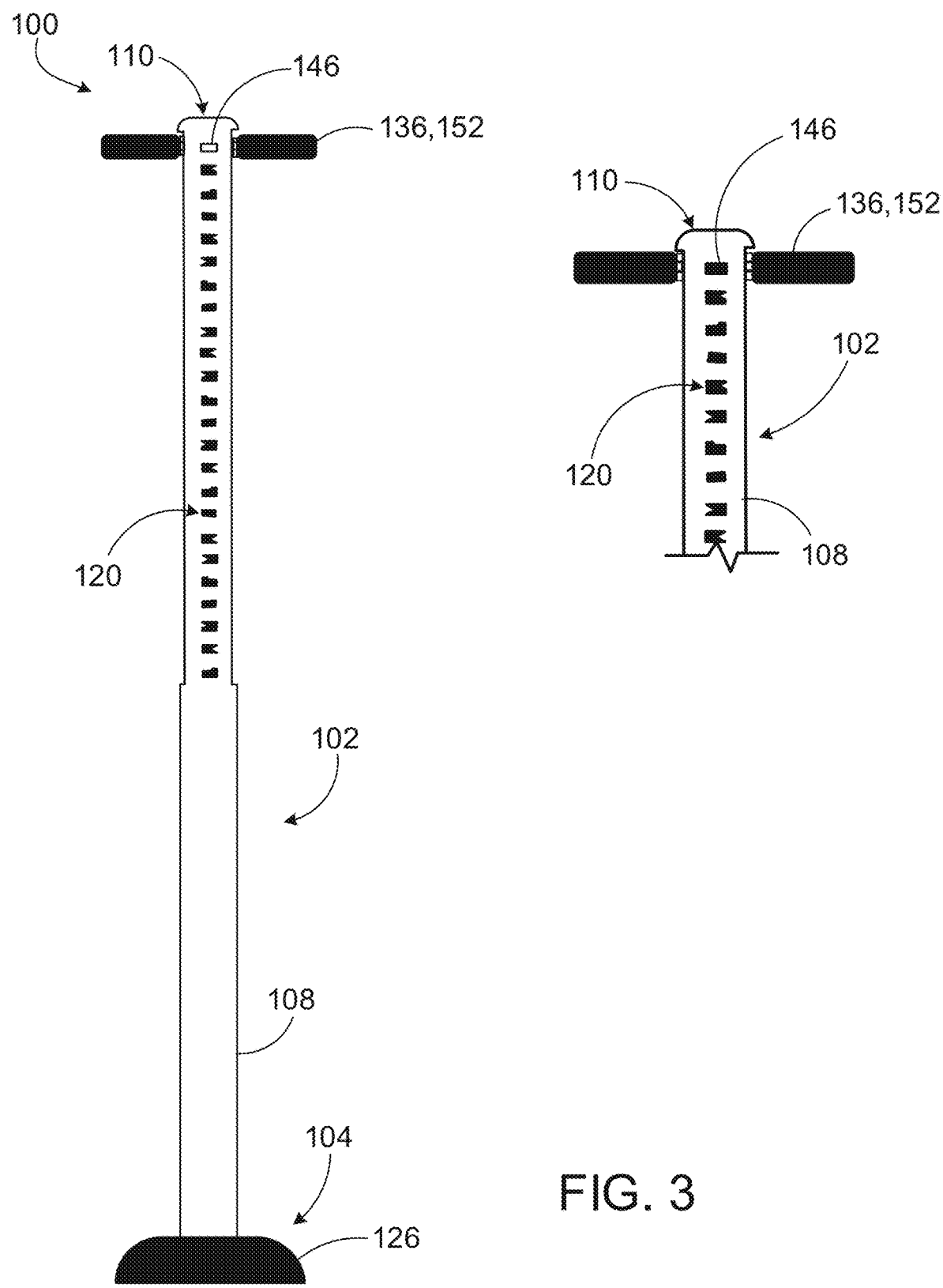
FIG. 3 is a rear view of the mechanical lift of FIG. 1.
Figure 4:
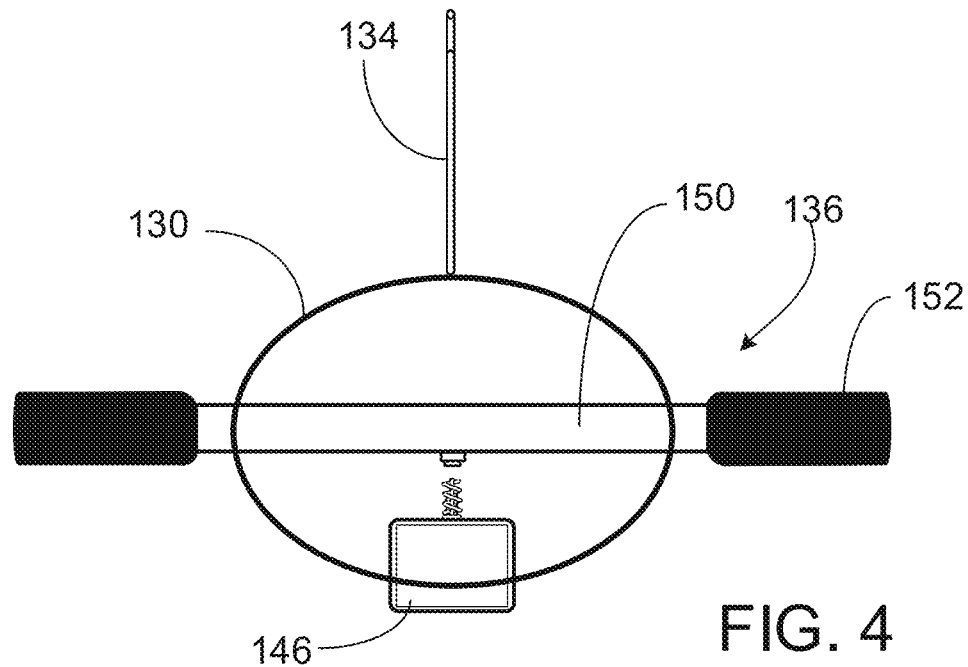
FIG. 4 is a top cutaway view of an adjustment block of the mechanical lift of FIG. 1, with a stopper of the mechanical lift in an extended position.
Figure 5:
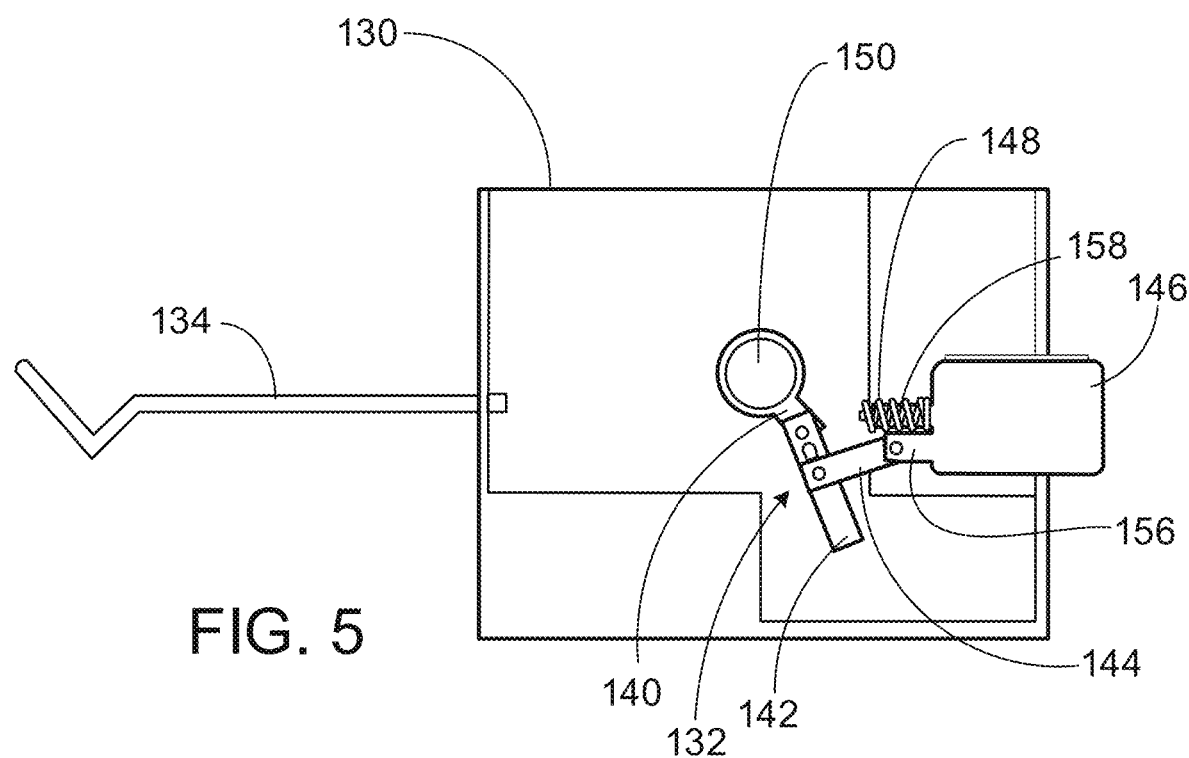
FIG. 5 is a side cutaway view of the adjustment block of FIG. 4, with the stopper in the extended position.
Figure 6:
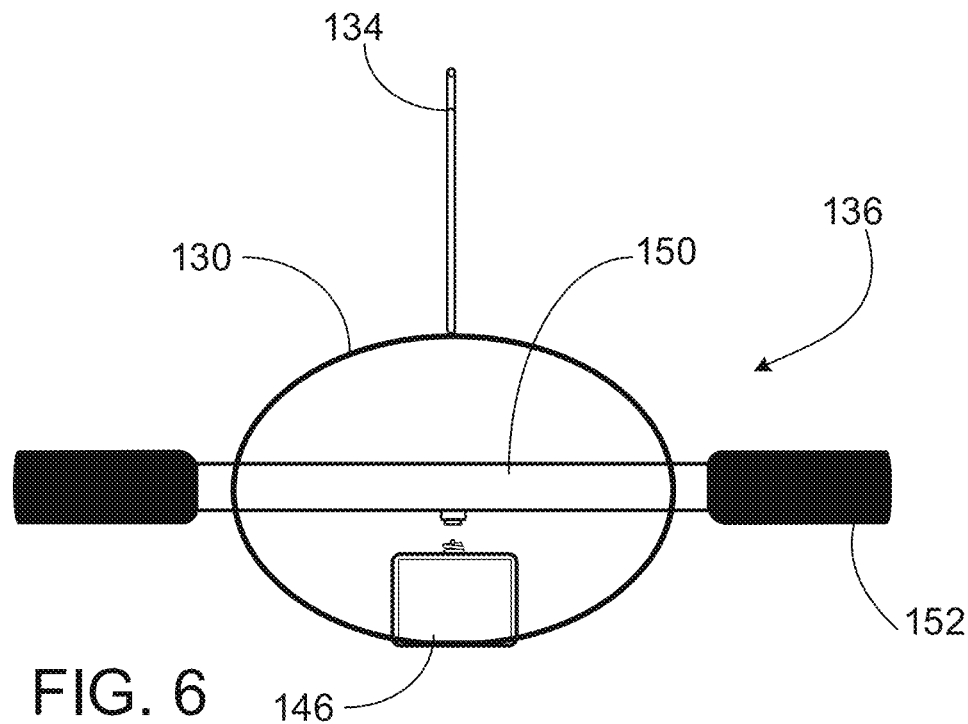
FIG. 6 is a top cutaway view of the adjustment block of FIG. 4, with the stopper in a retracted position.
Figure 7:
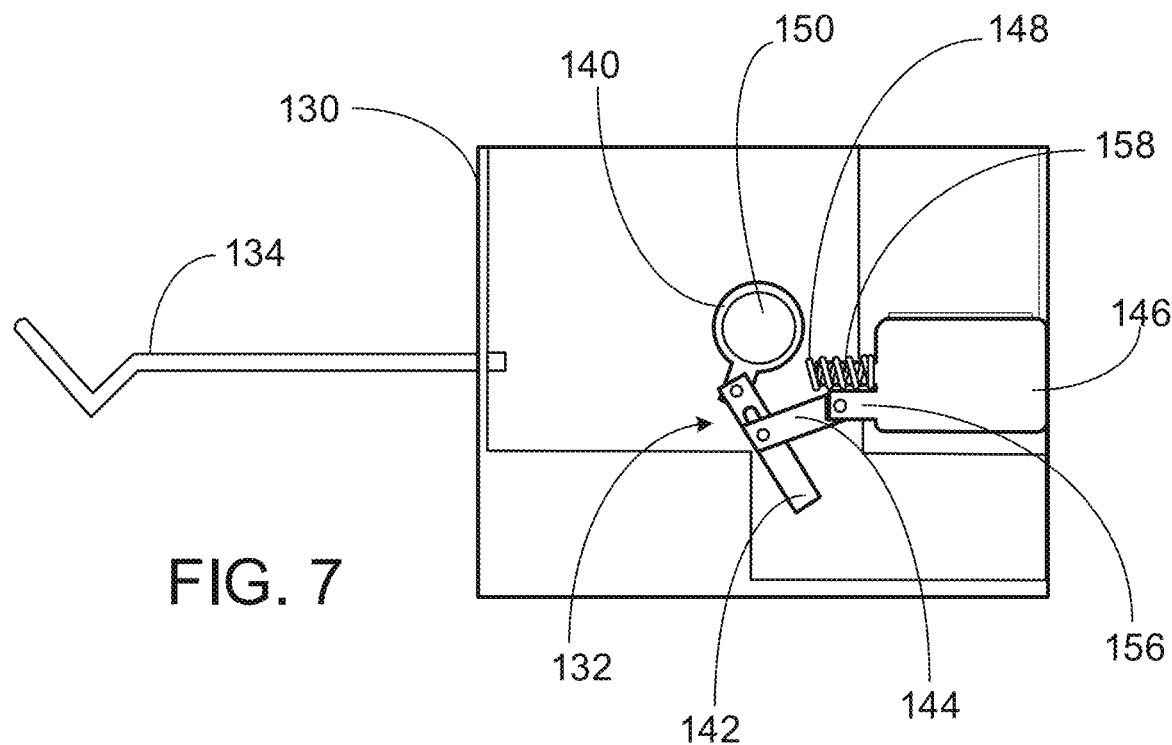
FIG. 7 is a side cutaway view of the adjustment block of FIG. 4, with the stopper of in the retracted position.
Figure 8:
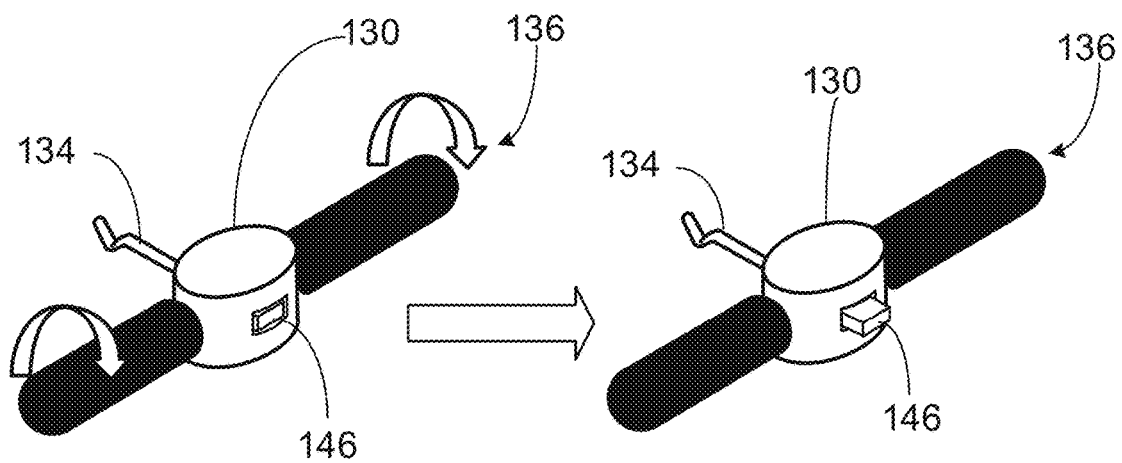
FIG. 8 is an illustration of extension of the stopper of the mechanical lift of FIG. 1 upon rotating a handle of the mechanical lift in a first direction.
Figure 9:
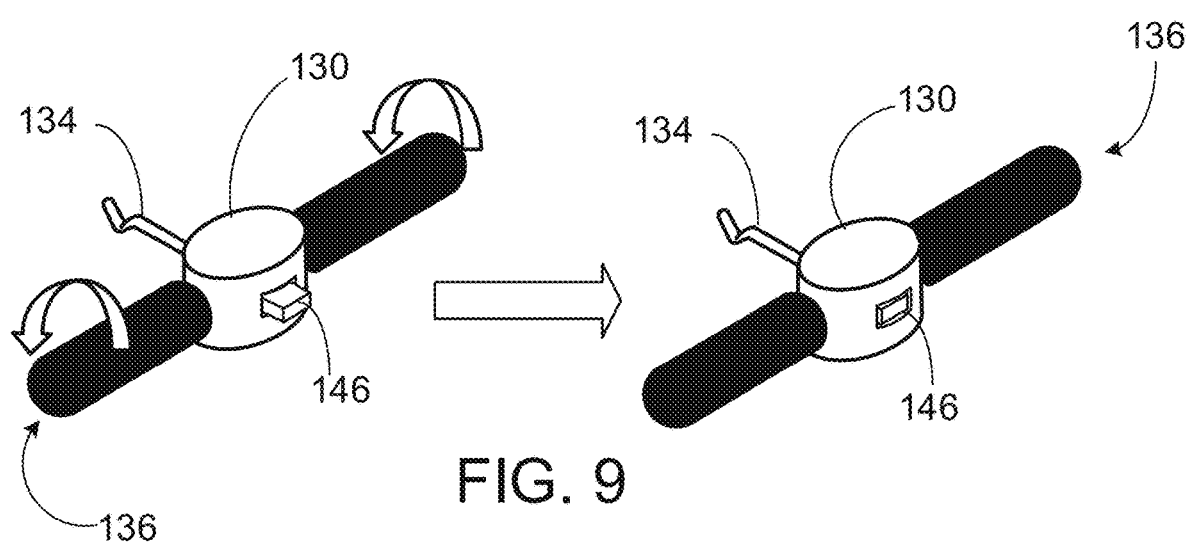
FIG. 9 is an illustration of retraction of the stopper of the mechanical lift of FIG. 1 upon rotating the handle of the mechanical lift in a second direction.

FIGS. 1-3 illustrate various views of a mechanical lift 100 that is designed to mechanically lift a container of fluid that is supported by the mechanical lift 100. For example, the mechanical lift 100 is a standing structure that may be embodied as an IV pole that mechanically raises a bag of medical fluid to prevent a user from having to physically lift the bag manually. Example medical fluids that may typically be contained in such a bag includes dialysis solutions and IV solutions.

The mechanical lift 100 includes a vertical housing 102 (e.g., a pole), a base 104 that supports the housing 102, a lifting mechanism 106 disposed within the housing 102, and a hook 134 for supporting a container of fluid. The housing 102 is an elongate, rigid structure with a round (e.g., ovular, square-round, or circular) cross-sectional shape. The housing 102 includes a hollow wall 108 that extends upward from the base 104 and a cap 110 (e.g., a ceiling) that closes the wall 108 at an upper end. An interior region 114 of the wall 108 houses the lifting mechanism 106. An upper section 112, the wall 108 defines two opposite lateral openings 116 (e.g., cutouts) through which components of the lifting mechanism 106 can be viewed and a front opening 118 through which the hook 134 passes.

The wall 108 also defines a vertical series of rear slots 120 that form height adjustment notches along the upper section 112. The lifting mechanism 106 can be discretely positioned at any selected slot 120 of the multiple slots 120, as will be discussed in more detail below. In some embodiments, the wall 108 defines 3 to 26 slots 120. The slots 120 may have a generally rectangular shape (e.g., as shown in FIG. 3) or have a different shape. The openings 116, 118 are oriented vertically, while the slots 120 are oriented horizontally. The wall 108 may optionally define an ornamental cutout pattern 124 (e.g., a logo) along a lower section 122 (e.g., as shown in FIG. 1) or at a different location.

The housing 102 is made of one or more relatively hard materials, such as aluminum or carbon fiber. The lower section 122 of the housing 102 (e.g., extending upward from the base 104) typically has a vertical length of about 80 cm to about 106 cm. The upper section 112 of the housing 102 (e.g., defining a vertical extent of the openings 116, 118, 120 and extending upward from the lower section 122) typically has a vertical length of about 80 cm to about 106 cm. Accordingly, the housing 102 typically has a total vertical length of about 160 cm to about 212 cm. The lateral openings 116 typically a width of about 3.5 cm to about 5.0 cm, and the front opening 118 typically has a width of about 1.0 cm to about 3.0 cm. The slots 120 are formed identically and are equally spaced apart from each other along the upper section 112. Each slot 120 typically has a height of about 0.7 cm to about 1.8 cm and a width of about 2.0 cm to about 3.5 cm. The slots 120 are typically spaced apart from each other by a regular distance of about 1.2 cm to about 4.0 cm (e.g., about 1.5 cm to about 3.8 cm).

Referring to FIGS. 1-7, the lifting mechanism 106 includes a compression spring 128 that resides within the interior region 114 of the housing 102, an adjustment block 130 that is attached to an upper end of the compression spring 128, a latch mechanism 132 carried by the adjustment block 130, and a handle 136 that extends laterally through the adjustment block 130. The hook 134 is securely attached to and extends forward from the adjustment block 130. The hook 134 is formed from a relatively strong material and is shaped and sized to support a mass (e.g., the container of fluid) of up to about 15 kg. The hook 134 typically has a length of about 3.5 cm to about 12.0 cm. Example materials from which the hook 134 may be made include stainless steel and aluminum.

Referring to FIGS. 4-7, the handle 136 includes a bar 150 that extends through the adjustment block 130 and two opposing hand grips 152 that are carried on the bar 150. In some embodiments, the hand grips 152 and the hook 134 may be coated with a fluorescently colored substance, layer, or material to provide visibility for easy location of the mechanical lift 100 in the dark. The latch mechanism 132 includes an anchor arm 140 that is fixed to the bar 150 such that the anchor arm 140 rotates as the handle 136 is rotated. The latch mechanism 132 also includes a slotted arm 142 that is pivotably coupled to the anchor arm 140 and an actuation arm 144 that is pivotably coupled to the slotted arm 142. The latch mechanism 132 further includes a stopper 146 this is slidable horizontally (e.g., forward and rearward) within the adjustment block 130.

The stopper 146 includes a main body 154 that is extendable outside of the adjustment block 130, an extension arm 156 that is pivotably coupled to the actuation arm 144 of the latch mechanism 132, and a coupling arm 158 that carriers a spring 148. The main body 154 of the stopper 146 has a generally rectangular cross-sectional shape and is sized to be engaged with and securely retained in a selected slot 120 when the stopper 146 is in an extended position, as shown in FIGS. 2 and 3. Due to the coupling between the handle 136 and the latch mechanism 132, twisting of the handle 136 (e.g., using the hand grips 152) results in a horizontal movement of the stopper 146 between the extended position and a retracted position in which an outer flat edge of the stopper 146 is substantially flush with an outer surface of the adjustment block 130 at a widest point of the adjustment block, as shown in FIGS. 4 and 6-8. In this manner, the coupling between the handle 136 and the latch mechanism 132 provides a manual locking mechanism. For example, in some embodiments, forward rotation of the handle 136 causes outward protrusion of the stopper 146, and rearward rotation of the handle 136 causes retraction of the stopper 146.

The compression spring 128 (e.g., an open-coil helical spring) is positioned within the interior region 114 along a central axis of the housing 102. In an extended configuration, the compression spring 128 extends the vertical length of the interior region 114 of the housing 102 up to the adjustment block 130. The compression spring 128 is calibrated to expand from a compressed configuration and support a predetermined mass. For example, if a patient's prescription requires usage of a 5 L bag of fluid, then the compression spring 128 is designed to exert the required amount of force to return to a substantially uncompressed length after the 5 L bag of fluid has been loaded on the hook 134 and while the stopper 146 is in the retracted configuration to allow free vertical motion of the adjustment block 130. In some embodiments, the compression spring 128 is made of stainless steel. In some embodiments, the compression spring 128 is rated to support a load of up to about 15 kg.

Figure 10:
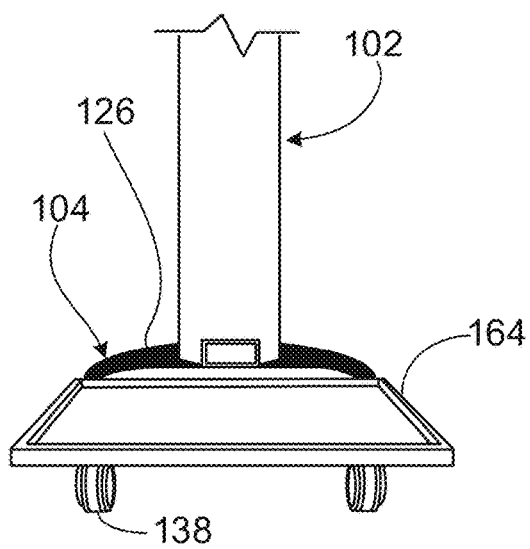
FIG. 10 is a perspective view of a base of the mechanical lift of FIG. 1.
Figure 11:
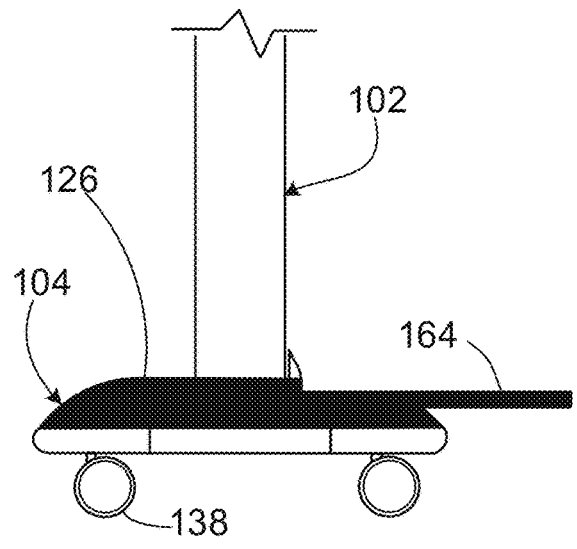
FIG. 11 is a side view of the base of the mechanical lift of FIG. 1.

Referring to FIGS. 10 and 11, the base 104 of the mechanical lift 100 includes a weighted platform 126 for supporting the other components of the mechanical lift 100, four lockable caster wheels 138 for rolling the mechanical lift 100, and an optional scale 164 for weighing the container of fluid if desired. The base 104 typically has a length of about 30 cm to about 40 cm, a width of about 30 cm to about 40 cm, and a total height (e.g., including the platform 126 and the caster wheels 138) of about 10 cm to about 13 cm. The platform 126 typically has a mass of about 1.5 kg to about 2 kg, while the mechanical lift 100 typically has a total mass of about 0.5 kg to about 1 kg. In some embodiments, the lowermost slot 120 in the housing 102 is located at a distance of about 0.9 m to about 1.1 m above a bottom end of the platform 126, and the uppermost slot 120 is located at a distance of about 1.9 m to about 2.0 m above the bottom end of the platform 126. Owing to the total height of the base 104 and the vertical length of the lower section 122 of the housing wall 108, the uppermost slot 120 in the housing 102 is typically positioned at a height of about 2.0 m to about 2.1 m from the floor, and the lowermost slot 120 in the housing 102 is typically positioned at a height of about 1.0 m to about 1.2 m from the floor. Such locations of the slots 120 allow for about 95% of the population to comfortably and easily access the vertical range of the slots 120.

Figure 12:
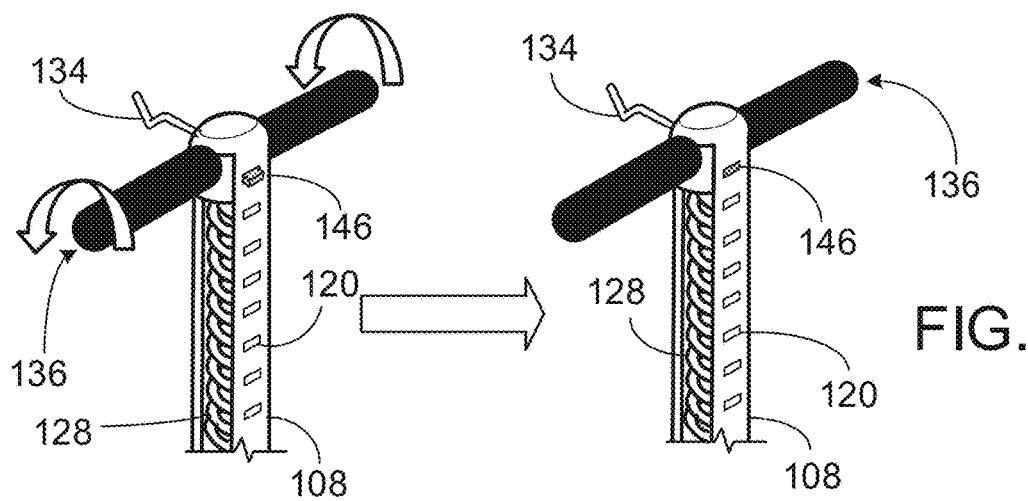
Figure 13:
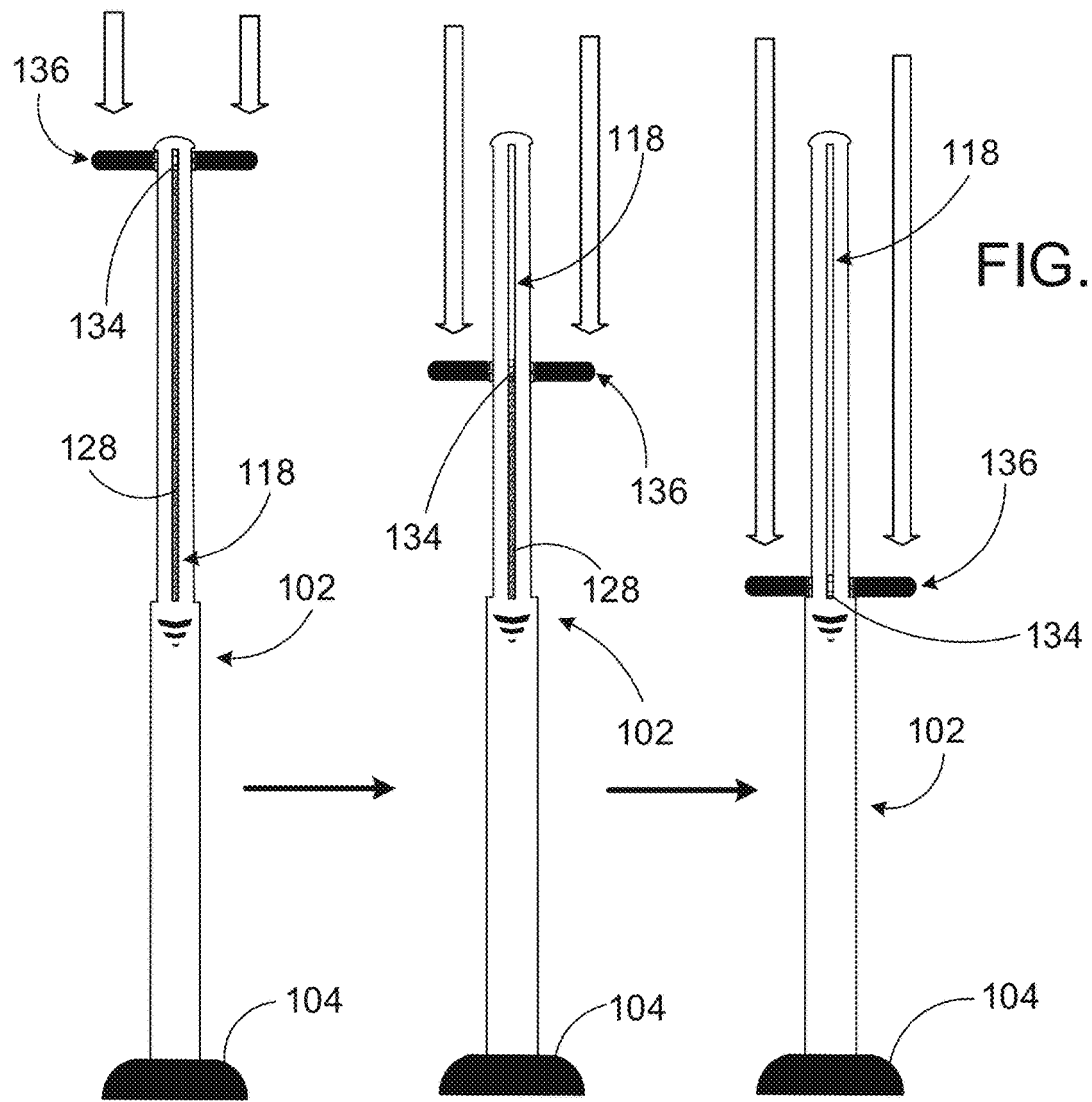

FIGS. 12-16 illustrate a method of operating the mechanical lift 100 to position a container 160 (e.g., a bag) of fluid 162 (e.g., to load the container 160 of fluid 162 on the mechanical lift 100). Referring to FIG. 12, the lifting mechanism 106 may be in an initial configuration in which the compression spring 128 is fully extended and the adjustment block 130 is locked in position with the stopper 146 in the extended configuration at the upper most slot 120. Referring to FIG. 12, the handle 136 is rotated forward by a user (e.g., a patient, the patient's family member, or a clinician) to retract the stopper 146 and accordingly unlock the latch mechanism 132. Referring to FIG. 13, with the stopper 142 in the retracted position, the handle 136 is pushed downward by the user until the adjustment block 130 reaches a slot 120 positioned at a height that is comfortable (e.g., near waist height or shoulder height) for the user to easily reach. The compression spring 128 has a stiffness (e.g., with a spring constant of about 5.5 N/m to about 7.0 N/m) that is low enough to allow the user to exert a downward force on the handle 136 with relative ease that is sufficient to move the handle 136 to the desired slot 120.

Referring to FIG. 14, once the handle 136 is located at the desired slot 120, the handle 136 is rotated rearwardly by the user to extend the stopper 146 through the slot 120. The latch mechanism 132 is accordingly locked, and the adjustment block 130 is secured in position. Referring to FIG. 15, the container 160 of fluid 162 is hung on the hook 134 by the user. The handle 136 is then is rotated forward again by the user to retract the stopper 146 and accordingly unlock the latch mechanism 132. Referring to FIG. 16, with the stopper 142 in the retracted position, the handle 136 is released by the user to allow the compression spring 128 to expand automatically to its uncompressed length. With the stopper 142 maintained in the retracted position, the compression spring 128 slowly extends upward to mechanically lift the adjustment block 130, carrying the hook 134 and the container 160 of fluid 162, to the uppermost slot 120 at the top of the housing 102. The handle 136 is then rotated rearwardly again by the user to extend the stopper 146 through the slot 120 to securely lock the adjustment block 130 in position.

The mechanical lifting functionality provided by the lifting mechanism 106 reduces muscle activity the user would otherwise undergo to lift the container 160. The functionality accordingly provides an ergonomic benefit in that it allows for improved posture and reduces the likelihood of lift-related injuries. The mechanical lift 100 is user-friendly in that it provides for easy lifting, hanging, and disposal of the container 160. In this regard, the design of the mechanical lift also reduces the probability that the user will drop a filled container 160 to the floor, which may lead to wasted medical fluids, damage to the floor, injury (e.g., as related to slipping on a wet floor or mechanical trauma to the user's foot), and associated costs.

While the mechanical 100 has been described and illustrated with respect to certain dimensions, sizes, shapes, arrangements, materials, and methods, in some embodiments, a mechanical lift that is otherwise substantially similar in construction and function to the mechanical lift 100 may include one or more different dimensions, sizes, shapes, arrangements, configurations, and materials or may be utilized according to different methods. Accordingly, other embodiments are also within the scope of the following claims.

What is claimed is:
1. A mechanical lift comprising:
a housing defining a series of vertical adjustment notches;
an adjustment block disposed within the housing;
a hook extending directly from the adjustment block and configured to support a hanging load;
a stopper supported by the adjustment block and movable between:
a retracted position in which the stopper is disposed within the adjustment block and is disengaged from the housing, and an extended position in which the stopper extends from the adjustment block and is engaged with a selected notch of the series of vertical adjustment notches of the housing to lock a vertical position of the adjustment block and the hook extending therefrom such that the hook is vertically aligned with the selected notch; and a spring disposed within the housing and exerting an upward force against the adjustment block to mechanically lift the adjustment block and the hook extending therefrom from a first vertical position at a first notch of the series of vertical adjustment notches to a second notch of the series of vertical adjustment notches when the stopper is in the retracted position.

2. The mechanical lift of claim 1, further comprising a handle supported on the adjustment block.

3. The mechanical lift of claim 2, wherein the handle is pivotably coupled to the stopper such that rotation of the handle causes movement of the stopper between the retracted position and the extended position.

4. The mechanical lift of claim 3, further comprising one or more pivotable arms that couple the handle to the stopper.

5. The mechanical lift of claim 1, wherein the series of vertical adjustment notches comprises a series of slots.

6. The mechanical lift of claim 5, wherein the stopper is configured to pass through the selected notch.

7. The mechanical lift of claim 1, wherein the housing defines an opening through which the adjustment block and the spring are viewable.

8. The mechanical lift of claim 1, wherein the hook extends from a first side of the adjustment block and the stopper extends from a second side of the adjustment block that is opposite to the first side.

9. The mechanical lift of claim 1, wherein the lowest notch of the series of vertical adjustment notches is located at a distance of about 0.9 m to about 1.1 m above a bottom end of the mechanical lift, and wherein the highest notch of the series of vertical adjustment notches is located at a distance of about 1.9 m to about 2.0 m above the bottom end of the mechanical lift.

10. The mechanical lift of claim 1, wherein the vertical adjustment notches of the series are equally spaced from each other by a distance of about 1.5 cm to about 3.8 cm.

11. The mechanical lift of claim 1, wherein the spring comprises a compression spring that is compressible to locate the adjustment block at the first notch.

12. The mechanical lift of claim 1, wherein the spring is calibrated to the hanging load.

13. The mechanical lift of claim 1, wherein the hanging load comprises a container of fluid.

14. The mechanical lift of claim 13, wherein the container of fluid comprises a bag of medical fluid.

15. The mechanical lift of claim 1, further comprising a platform that supports the housing.

16. A method of positioning a load, the method comprising:
providing a mechanical lift comprising a housing defining a series of vertical adjustment notches, an adjustment block disposed within the housing, a hook extending directly from the adjustment block and configured to support the load, a stopper supported by the adjustment block, and a spring disposed within the housing and exerting an upward force against the adjustment block;
moving the stopper to an extended position with respect to the adjustment block to engage the stopper with a first notch of the series of vertical adjustment notches of the housing to lock the adjustment block and the hook extending therefrom at a first vertical position of the first notch such that the hook is vertically aligned with the first notch;
hanging the load on the hook;
moving the stopper from the extended position to a retracted position within the adjustment block to disengage the stopper from the housing; and
extending the spring to mechanically lift the adjustment block and the load hanging from the hook from the first vertical position to a second vertical position of a second notch of the series of vertical adjustment notches.

17. The method of claim 16, wherein the mechanical lift further comprises a handle supported on the adjustment block, and wherein the handle is pivotably coupled to the stopper.

18. The method of claim 17, further comprising rotating the handle to move the stopper from the extended position to the retracted position.

19. The method of claim 16, further comprising moving the stopper to the extended position at the second vertical position to engage the stopper with the second notch to lock the adjustment block and the load hanging from the hook at the second vertical position.

20. The method of claim 16, further comprising:
moving the adjustment block downward to the first vertical position and compressing the spring after moving the stopper to the retracted position; and
locking the adjustment block and the hook extending therefrom at the first vertical position.

21. The method of claim 16, wherein the load comprises a bag of medical fluid.

22. A mechanical lift comprising:
a housing defining a series of vertical adjustment notches;
an adjustment block disposed within the housing;
a hook extending from the adjustment block and configured to support a hanging load;
a stopper supported by the adjustment block and movable between:
a retracted position in which the stopper is disposed within the adjustment block and is disengaged from the housing, and
an extended position in which the stopper extends from the adjustment block and is engaged with a selected notch of the series of vertical adjustment notches of the housing to lock a vertical position of the adjustment block and the hook extending therefrom;
a spring disposed within the housing and exerting an upward force against the adjustment block to mechanically lift the adjustment block and the hook extending therefrom from a first vertical position at a first notch of the series of vertical adjustment notches to a second notch of the series of vertical adjustment notches when the stopper is in the retracted position; and
a handle supported on the adjustment block, wherein the handle is pivotably coupled to the stopper such that rotation of the handle causes movement of the stopper between the retracted position and the extended position.

23. A mechanical lift comprising:
a housing defining a series of vertical adjustment slots;
an adjustment block disposed within the housing;
a hook extending from the adjustment block and configured to support a hanging load;
a stopper supported by the adjustment block and movable between:

a retracted position in which the stopper is disposed within the adjustment block and is disengaged from the housing, and an extended position in which the stopper extends from the adjustment block and is engaged with a selected slot of the series of vertical adjustment slots of the housing to lock a vertical position of the adjustment block and the hook extending therefrom, wherein the stopper is configured to pass through the selected slot; and a spring disposed within the housing and exerting an upward force against the adjustment block to mechanically lift the adjustment block and the hook extending therefrom from a first vertical position at a first slot of the series of vertical adjustment slots to a second slot of the series of vertical adjustment slots when the stopper is in the retracted position.

24. A mechanical lift comprising:

a housing defining a series of vertical adjustment notches;

an adjustment block disposed within the housing;

a hook extending from the adjustment block and configured to support a hanging load;

a stopper supported by the adjustment block and movable between:
- a retracted position in which the stopper is disposed within the adjustment block and is disengaged from the housing, and
- an extended position in which the stopper extends from the adjustment block and is engaged with a selected notch of the series of vertical adjustment notches of the housing to lock a vertical position of the adjustment block and the hook extending therefrom; and a spring disposed within the housing and exerting an upward force against the adjustment block to mechanically lift the adjustment block and the hook extending therefrom from a first vertical position at a first notch of the series of vertical adjustment notches to a second notch of the series of vertical adjustment notches when the stopper is in the retracted position, wherein the housing defines an opening through which the adjustment block and the spring are viewable.

25. A method of positioning a load, the method comprising:

providing a mechanical lift, the mechanical lift comprising:
a housing defining a series of vertical adjustment notches, an adjustment block disposed within the housing, a hook extending from the adjustment block and configured to support the load, a stopper supported by the adjustment block, a spring disposed within the housing and exerting an upward force against the adjustment block, and a handle supported on the adjustment block, the handle being pivotably coupled to the stopper;

moving the stopper to an extended position with respect to the adjustment block to engage the stopper with a first notch of the series of vertical adjustment notches of the housing to lock the adjustment block and the hook extending therefrom at a first vertical position of the first notch;

hanging the load on the hook;

moving the stopper from the extended position to a retracted position within the adjustment block to disengage the stopper from the housing; and extending the spring to mechanically lift the adjustment block and the load hanging from the hook from the first vertical position to a second vertical position of a second notch of the series of vertical adjustment notches.

* * * * *